United States Patent
Vallejo, Jr. et al.

(10) Patent No.: US 10,458,916 B2
(45) Date of Patent: Oct. 29, 2019

(54) RAPID TESTS FOR THE DETECTION OF INHIBITORS OF ENZYMES AND HUMAN EXPOSURE TO THE SAME

(71) Applicant: ANP Technologies, Inc., Newark, DE (US)

(72) Inventors: Yli Remo Vallejo, Jr., Newark, DE (US); David Milunic, Newark, DE (US)

(73) Assignee: ANP Technologies, Inc., Newark, DE (US)

( * ) Notice: Subject to any disclaimer, the term of this patent is extended or adjusted under 35 U.S.C. 154(b) by 202 days.

(21) Appl. No.: 14/827,674

(22) Filed: Aug. 17, 2015

(65) Prior Publication Data

US 2015/0353987 A1 Dec. 10, 2015

Related U.S. Application Data

(63) Continuation of application No. 14/004,383, filed as application No. PCT/US2012/030196 on Mar. 22, 2012, now abandoned.

(60) Provisional application No. 61/466,884, filed on Mar. 23, 2011.

(51) Int. Cl.
  *C12Q 1/44* (2006.01)
  *G01N 21/64* (2006.01)
  *C12Q 1/46* (2006.01)

(52) U.S. Cl.
  CPC ............ *G01N 21/6486* (2013.01); *C12Q 1/44* (2013.01); *C12Q 1/46* (2013.01)

(58) Field of Classification Search
  CPC ..... C12Q 1/44; C12Q 1/46; C12Q 1/26; C12Q 1/42; C12Y 301/01001; C12Y 301/01007; G01N 21/6486; G01N 2333/916; G01N 33/558
  See application file for complete search history.

(56) References Cited

U.S. PATENT DOCUMENTS

| | | | |
|---|---|---|---|
| 6,221,625 B1 * | 4/2001 | Ashihara | G01N 33/542 422/424 |
| 6,406,876 B1 | 6/2002 | Gordon et al. | |
| 7,897,360 B2 | 3/2011 | Song | |
| 9,012,110 B2 | 4/2015 | Lowe et al. | |
| 2005/0089926 A1 | 4/2005 | Taylor et al. | |
| 2006/0286548 A1 * | 12/2006 | Liposky | G01N 33/6842 435/5 |
| 2010/0178204 A1 | 7/2010 | Yin et al. | |

FOREIGN PATENT DOCUMENTS

| | | | |
|---|---|---|---|
| EP | 1175509 | 9/2006 | |
| WO | WO 0065081 A2 * | 11/2000 | ............... C12Q 1/34 |
| WO | 2010041078 | 4/2010 | |
| WO | WO 2010041078 A1 * | 4/2010 | ............ C12Q 1/005 |

OTHER PUBLICATIONS

Aparna et al. (2010) American-Eurasian J. Agric. and Environ. Sci 7(6): 657-670. (Year: 2010).*
Ono et al., "A highly . . . IgE," J Imm Meth 272:211-218, 2003.
Cho et al., "Development . . . Fenthion," J Agri Food Chem 51:7854-7860, 2003.
Mason et al., "Butyrylcholinesterase . . . behavior," Biochim Biophys Acta 1597:229-243, 2002.
Adams et al., "Poly(2-oxazolines) . . . contexts," Adv Drug Del Rev 59:1504-1520, 2007.

* cited by examiner

*Primary Examiner* — Lisa J Hobbs
(74) *Attorney, Agent, or Firm* — Gann G Xu; MDIP LLC (57) ABSTRACT

A device and method for the rapid on-site detection of inhibitors of enzymes, such as, acetylcholinesterase is described where the device contains 2 reaction zones containing a reporter enzyme substrate. One reaction zone is for the test sample while the other is for an onboard negative control. Sample and control fluids are preincubated with the enzyme in separate reaction containers, then an aliquot of each reaction mixture is added to designated reaction zones on the test device. A purpose-built reader or an illuminating device, such as, containing an incandescent light source, a diode, a UV light source or any other illumination source that is suitable for the reporter or mere visualization is used to determine the level of reporter.

28 Claims, 4 Drawing Sheets

Negative Result Under UV light  Positive Result Under UV light

Figure 8 .

RAPID TESTS FOR THE DETECTION OF INHIBITORS OF ENZYMES AND HUMAN EXPOSURE TO THE SAME

FIELD OF THE INVENTION

The present invention relates in part to rapid on-site detection methods of acetylcholinesterase-inhibiting compounds and the rapid detection of systemic poisoning in individuals exposed to these inhibitors. The use of pesticides has contributed to significant improvement in agricultural efficiency and productivity over the last 60 years and in the control and eradication of disease-bearing insects and other predators. However, the overuse of such compounds has led to the contamination of soil and, through agricultural runoff, drinking water sources. The organophosphate and carbamate classes of pesticides are examples of such compounds. These pesticides owe their effectiveness to their ability to inhibit the neurotransmitter enzyme acetylcholinesterase (AChE), which regulates nerve impulses in many life forms, including humans. When this enzyme is inhibited by these pesticides, the victim begins to suffer from bradycardia, hypotension, hypersecretion, bronchoconstriction, GI tract hypermotility, and decreased intraocular pressure. Morbidity progresses to death in many cases as exposure levels are increased. Many nerve agents used in chemical warfare are also acetylcholinesterase inhibitors. Examples of these are sarin, soman, tabun, VX, VE, VG and VM. Exposure to or ingestion of pesticides and related neurotoxins has also been linked to chronic illnesses, such as, depression and Parkinson's disease. The management of worker exposure and of the effects on the general population requires methods that provide ready detection of such exposure by testing blood, plasma, serum or other biological fluids, or samples for the inhibition of the target enzymes.

BACKGROUND OF THE INVENTION

The detection of AChE inhibitors has been conducted using colorimetric methods that are based on decrease in color development by a primary or secondary substrate after exposure of the enzyme to a liquid sample containing an inhibitor. An example of such is the colorimetric method commercialized by Abraxis which uses Ellman's color reagent as an indicator substrate. That method tests the activity of a measured amount of enzyme after it has been exposed to a water sample potentially containing an inhibitor. After such exposure, the enzyme is reacted with its primary substrate acetylthiocholine. Active enzyme will hydrolyze acetylthiocholine to thiocholine which in turn reacts with dithio-bis-nitrobenzoate to produce an orange-colored product, 5-thio-2-nitrobenzoate.

That method, though widely used, is complex, a standard curve is needed, numerous fluid transfer pipetting steps are necessary, and a multiplicity of reaction vessels are used. In addition, the enzyme is inhibited by many organophosphates in vivo only after the inhibitor undergoes a physiological oxidation (Mahajna and Casida, 1998). Hence, a sample pretreatment step using an oxidizing agent, such as, bromine or hypochlorite followed by a quencher to neutralize excess unreacted oxidizer is required. Only by pre-oxidizing the sample can most organophosphates be detected by such methods.

Although such assays represent the current standard in AChE inhibitor detection, Ellman's Reagent-based methods are not converted readily to rapid on-site testing because of the methodological complexity, the numerous steps and reaction vessels required and the need to keep heat-labile reagents refrigerated.

Other methods to detect such inhibitors are laboratory-based liquid or gas chromatography methods coupled with mass spectrometry which rely on elution profiles for identification.

Rapid methods are also required to determine whether an individual has been exposed to neurotoxins to administer countermeasures and antidotes in timely fashion. Occupational exposure to pesticides, nerve agents and other cholinesterase-inhibiting metals is a common risk to individuals employed in the chemical, agricultural and mining industries and in the armed forces. Inhalation and absorption through unprotected skin are the most common modes of exposure.

Current methods for determining exposure consist of laboratory procedures based on the use of Ellman's Reagent. Approved methods include the Michel, microMichel, pH stat, Ellman and micro-Ellman assays, as well as certain variations of those assays.

Hence, there is a need for a simplified and rapid point of use assay. The instant invention addresses those shortcomings. The assay of interest can be configured to test plasma esterase, such as, cholinesterase, activity using, for example, plasma or serum obtained via venipuncture or diluted fingerstick blood, or environmental samples.

SUMMARY OF THE INVENTION

To overcome the shortcomings in the art of detecting esterase, such as, cholinesterase, such as, acetylcholinesterase (ACNE) inhibitors, the instant invention relates to a simplified self-calibrated rapid test employing a modular device, referred to as a ticket, containing two reaction zones in the form of wells that hold dry absorbent pads coated with a substrate of the enzyme, where the substrate can be a reporter (herein identified also as a substrate reporter or a reporter substrate), such as, a primary fluorogenic enzyme substrate. In addition, the test uses two separate reagent containers, both containing a fixed uniform amount of enzyme. To one container is added a uniform volume of a negative control fluid, such as, water, sample; in the other container is added the same uniform volume of an unknown fluid, such as, water, sample. The fluid sample can be, for example, a body fluid, such as, blood, which may be separated, treated or diluted, for example, or an environmental fluid sample, such as, water, which can be any water for human consumption, such as, processed drinking water, source water from natural and man-made or artificial bodies of water, such as, ponds and wells; lakes, rivers, oceans, water-based or water/organic washes or extracts of edible products, such as, fruits, vegetables, produce, meats and seafood, a dissolved or soluble sample of a wipe, swipe or an extract from a sampling of a suspected contaminated surface. A wash of an edible product comprises a liquid exposed to an edible product. A wipe or swipe comprises an absorptive or adsorptive material exposed to a surface, which absorptive or adsorptive material is exposed or suspended in a liquid and that liquid is used in a device and method of interest. The liquids dissolve any dried reagents or dilute any liquid reagents in each container. After gentle mixing, both containers are allowed to stand for a sufficient period of time so as to allow any inhibitors in the test sample to interact with and to deactivate the enzyme. A measured and uniform aliquot of each reaction mixture is then added to one of the two wells on the ticket. The ticket will have one well labeled for the control sample, such as, a water, and the other labeled for the test sample. Given a sufficient amount of time, the active enzyme in each mixture will react with the dried substrate in the well to generate a fluorescent signal. A comparison of the fluorescence generated in the test well with that generated in the control well determines the presence or absence of an inhibitor. In the case of an inhibitor present in the test sample, the test well will show measurably less fluorescence than does the control well. In the case of no inhibitor in the test sample, both wells will show the same level of fluorescence within a statistically established variation range. The fluorescence can be measured, for example, using a purpose-designed handheld reader with onboard algorithms that can calculate and display, for example, a ratio of the signal in the test well to the signal in the control well. Such an algorithm can use any channel of measured fluorescence (red, green, blue, hue, luminescence, saturation) that quantitatively represents the difference between the two wells. Alternatively, a handheld fluorescence flashlight holding light emitting diodes (LEDs) in the appropriate wavelength, can also be used to visually determine a difference between the two wells.

The requirement to oxidize the sample to detect organophosphates that are inhibitory only in vivo can be overcome by using a separate enzyme whose mode of activity is similar to AChE and can be inhibited by organophosphates without oxidation. Such an enzyme, for example, is carboxylesterase (CE), which is inhibited by unoxidized organophosphates. Both AChE and CE react with the same substrates.

Hence, the materials and methods of interest can relate to a modular test device for the detection of inhibitors of an enzyme comprising two reaction zones; 1) each reaction zone comprising a porous matrix comprises an immobilized substrate; 2) separate from the device, two reaction containers contain an enzyme in a measured and uniform amount; 3) a test sample fluid potentially containing an enzyme inhibitor is added in a measured uniform volume to one of the two reaction containers, and the same measured uniform volume of a negative control fluid is added to the other reaction container, then the containers are mixed to create a homogeneous reaction mixture in each container, and optionally allowing each container to incubate for a sufficient amount of time to allow any inhibitor to interact with the enzyme; 4) a measured and uniform aliquot of each reaction mixture from 3) then is added to separate reaction zones on the test device and the enzyme contained in each reaction mixture is allowed to interact with the substrate contained in each reaction zone; 5) the enzyme in each reaction mixture reacts with the substrate in each reaction zone to generate a measurable signal, such as, fluorescence or color; 6) wherein, a test sample containing inhibitor generates a lower or different signal on its test zone as compared to the signal of the control fluid; and 7) the test device then is read, for example, visually or in a reader to measure the reporter, for example, fluorescence or color, generated in each reaction zone; 8) wherein the reader can display a metric, such as, a positive or negative result based on a statistically determined ratio value cutoff, or a transformed metric, such as, the ratio value defined as the measured signal of the test reaction zone divided by the measured signal of the negative control fluid reaction zone; or 9) alternatively, using a flashlight or other illumination device, such as, an incandescent light source, a diode, a UV light source or any other illumination source that is suitable for the reporter used, generating illumination at specific wavelengths tuned to detect the reporter to enable human visualization of results on the test device. The reaction containers are separate from the modular test device, or ticket, which in turn, can be separate from the reader, although the ticket and the reader can be configured so that the ticket can be inserted into in whole or in part into the reader to enable the reader to detect reporter in the reaction zones. The test can be conducted with concurrently tested control samples, one or plural control samples, and which can comprise a negative control which would yield high levels of reporter as the enzyme would be free to act on the substrate; or can comprise a positive control which would yield low levels of reporter as the inhibitor would prevent enzymic activity on the reporter substrate, and so on. For example, plural wells can be configured to provide a titration to provide a more quantitative determination.

In other embodiments, the disclosure can relate in part to a device comprising an enzyme from the esterase family, including acetylcholinesterase, butylcholinesterase, carboxylesterase, among others.

Also, the disclosure can relate in part to a device comprising N-methylindoxyl acetate (NMI) as a fluorogenic substrate for esterases.

The disclosure can relate in part to a device for rapid, on-site detection of potentially harmful inhibitors of acetylcholinesterase including organophosphate, organothiophosphates and organophosponate pesticides and toxicants, carbamate pesticides, nerve agents, among others.

The disclosure can relate in part to a device specifically for the detection of acetylcholinesterase inhibitors of the organophosphate, organothiophosphate and organophosphonate classes, which device does not require oxidation of the test sample. In embodiments, a device comprises a carboxylesterase (CE) in place of or in addition to an acetylcholinesterase. Thus, the reaction containers do not contain an oxidizing agent, that is, the reactions containers are free of any oxidizing agent, and there is no need for oxidation of any inhibitor prior to assay.

The disclosure can relate in part to a system which combines two enzymes in order to detect all acetylcholinesterase inhibitors without the need to oxidize the sample. An enzyme such as AChE reacts strongly with non-organothiophosphate inhibitors such as carbamate pesticides, but reacts weakly with non-oxidized organothiophosphates. Enzymes such as CE do react strongly with organothiophosphates, but react weakly with carbamates. The detection system disclosed can therefore comprise two sets of enzyme reagents, one using, for example, an esterase which may require an oxidized inhibitor, such as, AChE, and the other enzyme being one which does not require an oxidized inhibitor, such as, CE. Both sets of reagents are reacted with control and test fluid, such as, water, samples as previously described. Each enzyme will then use tickets that contain the same reporter, such as, a fluorogenic primary substrate. The assay can comprise one ticket for each enzyme, or each well can comprise both enzymes. Alternatively, a modular device can be configured to comprise more than two wells so that individual enzymes can be sited in individual wells in a single test device. A positive result with one or both enzymes indicates the presence of a cholinesterase inhibitor.

The instant invention allows the detection of inhibitors, including those that belong to both the organophosphate and carbamate classes of compounds, in a simplified manner, without the required oxidation and quenching steps associated with many organophosphates and without the need to set up standard curves. Consequently, there are fewer reagents and vessels, as well as steps to practice the method, and the time to result is significantly reduced.

The instant invention can be applied to the detection of inhibitors of any enzyme. It is not limited to fluorescence as the measured signal, but can also use colorimetric substrates or reaction partners as appropriate.

The time to result using the instant invention can be shortened, for example, by heating the reaction vials containing the enzyme and the test or control samples and/or the test tickets following addition of the reaction mixtures. Heat sources can comprise, among others, water baths, incubators, heating blocks, ovens, exothermic reactions and other heat energy generators. Other means for accelerating reaction kinetics include incorporating reagents in the reaction mixture that facilitate or to accelerate reaction kinetics, that is, reaction between any inhibitor and the enzyme, such as, water soluble polymers such as polyethylene glycol (PEG), polyethyleneoxide (PEO), poly(vinylalcohol), poly(vinylpyrrolidone), polyoxazoline, polymethyloxazoline, polyethyloxazoline, salts and other solutes that can increase liquid phase activity of reactive molecules.

To overcome the limitations in the art of measuring the depression of cholinesterase activity in exposed individuals, the instant invention can also be used to determine whether enzyme, such as, cholinesterase, activity in an individual has been lowered due to exposure to inhibiting compounds. Using the test ticket previously described to comprise two reaction zones holding dried pads containing a reporter, such as, a fluorogenic or a chromogenic substrate, a rapid method to determine if an individual has been exposed to a neurotoxin is described comprising adding a body fluid, such as, plasma, saliva, serum, tears and so on, which may be separated or diluted, a tissue or cell wash or medium, such as, a tissue culture medium, a tissue storage medium and so on, or diluted whole blood in one reaction zone and comparing the signal developed therein to that developed in the other control reaction zone to which has been added the a sample, such as, plasma, serum, or whole blood of the individual collected prior to potential exposure, or a standard negative control solution. The control can be an enzyme, such as, a cholinesterase, at a concentration that will generate signal corresponding to the lower limit of the normal range of total cholinesterase activity in humans.

In embodiments, the device and method of interest can comprise direct addition of a sample and a control sample each to a well of a device of interest without or in the absence of mixing in a separate reaction vessel or container. The samples comprise an experimental sample suspected of exposure to an inhibitor and the control comprises a sample prior to exposure to an inhibitor, a known positive control or a known negative control. The sample can be a biological fluid obtained from an animal or a human, an environmental sample, such as, a water sample, and so on.

BRIEF DESCRIPTION OF THE FIGURES

The following descriptions of the figures relate to non-limiting examples that depict various embodiments exemplifying the present invention.

FIG. 1 depicts the test procedure for the detection of enzyme inhibitors, for example, a water sample. In this case, the enzyme is acetylcholinesterase. A fixed uniform volume of an unknown water sample to be tested is used to reconstitute a reagent bottle containing the enzyme. The control negative water is added using the same fixed volume to another reagent bottle containing enzyme. After mixing and an incubation period, a fixed uniform aliquot of each reaction mixture is added to its designated well, labeled C for control, T for test sample. After allowing a sufficient amount of time for the enzyme in each reaction mixture to react with the substrate in the wells, the fluorescence generated is measured on the handheld reader.

FIG. 2 shows the components of a rapid test system for the detection of enzyme inhibitors. The black ticket (1) contains two wells each containing dried substrate. Two reagent vials are provided each containing the same amount of lyophilized enzyme. One reagent vial will be reconstituted by the negative control water in the bottle provided (3), the other vial will be reconstituted by the test sample. The fluorescence developed on the ticket is measured on the handheld reader (4).

DETAILED DESCRIPTION OF THE INVENTION

The instant invention can be applied to the detection of an inhibitor of an enzyme and to the detection of a chemical that on exposure to a reaction partner can generate a measurable signal such as color, fluorescence or luminescence. The instant invention relates to a rapid test for discerning exposure to inhibitors of an enzyme, such as, esterase, such as, cholinesterase, such as, acetylcholinesterase-inhibiting compounds.

A key feature of the invention is the immobilization of the substrate on a porous matrix in a reaction zone to which a reaction mixture of the enzyme and test sample suspected of containing an inhibitor is added as the last fluid transfer step. By placing the enzyme in a reaction container outside of the test device, a non-obvious improvement in sensitivity is attained by the ability of the sample to inhibit the enzyme before the initiation of the substrate reaction.

For the purposes of non-limiting description of the invention, a detailed description of the rapid test for esterases is provided. Esterases are essential for normal nervous system function. Some toxins act by inhibiting esterase activity, such as, cholinesterase, such as, acetylcholinesterase activity. Depressed AChE activity causes, for example, aberrant synapse function. Thus, acetylcholinesterase (AChE) is an enzyme that degrades (through its hydrolytic activity) the neurotransmitter, acetylcholine, producing choline and an acetate group. AChE can be found at neuromuscular junctions and cholinergic nervous system, where AChE activity serves to terminate synaptic transmission. AChE is found in all animal species. As a reagent, AChE can be obtained and purified from any of several sources such as insects, eels, cows, and pigs. AChE also is available in recombinant form. The following examples exemplify the use of AChE inhibitors.

Carboxylesterase (CE) belongs to the family of carboxylic ester hydrolases which are widely found in nature. The enzyme catalyzes the hydrolytic cleavage of the ester bond in a carboxylic ester to form an alcohol and a carboxylic acid. This is the exact same hydrolysis reaction catalyzed by AChE when it reacts specifically with acetylcholine. As a reagent, CE can be isolated from many sources such as bacilli, rabbits, and pigs.

Both AChE and CE have common substrates, one of which is N-methylindoxyl acetate (NMI), which when hydrolyzed, produces acetic acid and N-methyl-3-hydroxyindole, which emits fluorescence on exposure to UV radiation at 380 nm.

To detect potentially harmful compounds that can inhibit AChE, a test procedure involves exposing a measured limiting amount of AChE to the sample that potentially contains the inhibitor. Inhibitor molecules in the sample can interact with the active sites of the enzyme and deactivate the enzyme. Subsequent reaction with a substrate reporter will show reduced enzyme activity (for example, lower fluorescence signal) when compared to a non-inhibited enzyme.

For the purposes of the invention as relating to esterases, such as, AChE, inhibitors can be classified as carbamates, organophosphates, organothiophosphates, organophosphonates, their derivatives and other compounds that can attach themselves to the serine hydroxyl group of the active site on acetylcholinesterase. That reaction blocks the neurotransmitter, acetylcholine, from interacting with the enzyme and resulting in cholinergic hyperactivity and loss of neurotransmitter control of the nervous system.

Most of the compounds that inhibit AChE do so without the need for metabolic transformation or chemical change. Certain organophosphates, however, do not exhibit inhibitory activity in vitro but do so in vivo only after a physiological oxidation of the phosphate moiety has occurred, such as, with organothiophosphates that require the thiophosphate group to undergo in vivo oxidation to a phosphate group. An example is methamidophos which is not detectable by such methods unless oxidized. Test methods have therefore always required a sample preparation step involving oxidation with a follow-on quenching of the unused oxidizing agent. Hence, the invention relates in part to a method that obviates the need for oxidation and quenching. Thus, the reactions vessels or containers do not contain or are free of an oxidizing agent so that incubating the sample and the enzyme occurs in the absence of an oxidizing agent.

The invention can comprise a system or testing system for detection of enzyme inhibitors comprising, in part, a device of such dimensions as to be handheld, which device contains two separate and exclusive reaction zones each containing a porous matrix that can absorb fluid. The same porous matrix is used for both reaction zones. The porous matrix is treated with a solution of the substrate such that on drying, substrate molecules are non-covalently attached to the porous matrix, that is, the substrate is immobilized on or affixed to the porous matrix. Enzyme substrates of interest are those that serve a reporter function and in some embodiments, the reporter is one which can be readily detected by a device or by mere visual inspection, which can be, for example, fluorogenic substrates that yield a fluorescence that can be visualized with the unaided eye, such as, NMI, chromogenic substrates that yield a detectable or visible color, or luminogenic substrates. Reaction zones will contain such porous matrices that have been uniformly treated with substrate such that one reaction zone is similar to the other in terms of the total amount of dry substrate contained. Examples of porous matrices include membranes, celluloses, glass fibers, cotton, nylon, composites and spun polymers, among others. Hence, an aliquot of a sample is added to the enzyme solution and then an aliquot of that solution is added to the reaction zone comprising the immobilized substrate of the ticket.

One reaction zone is designated for the test sample while the other is specified for a negative control. The zones can be labeled accordingly on the test device.

The test device is of such size and proportion as to compatibly fit in receptacle in a purpose-built reader which detects the reporter. The reader can be of such size and proportions as to be handheld. The test device can be inserted into a designated receptacle in this reader such that the test zones are efficiently exposed to light sources at the excitation wavelength of the product of the enzyme-substrate reaction and a camera or similar light or signal-gathering device that can measure the intensity of the emitted signal. An alternative design can use a chromogenic substrate that can be measured at the wavelength maximum of the enzyme-substrate reaction product.

Hence, the invention can relate in part to a test system for detecting enzyme inhibitors comprising: a) a device comprising two reaction zones, each reaction zone comprising a porous matrix comprising an immobilized substrate of said enzyme, wherein said substrate is a reporter for activity of said enzyme; b) separate from the device, a reaction container comprising said enzyme, and c) separate from the device, a reader that detects said substrate.

In some circumstances, the test system can relate to one where the enzyme comprises an esterase. Examples of esterases include acetylcholinesterase, butylcholinesterase or carboxylesterase. In some embodiments, the test system is one where the substrate comprises an N-methylindoxyl acetate (NMI). In certain embodiments, the test system detects inhibitors such as, an organophosphate, an organothiophosphate, an organophosphonate or a carbamate. Other inhibitors include a pesticide, a toxicant or a nerve agent. Advantageously, the test system of interest does not require oxidation of a test sample.

Hence, the invention can relate in part to a method for detecting an inhibitor of an enzyme comprising: a) adding an aliquot of a sample to a reaction container comprising said enzyme, and in a separate second reaction container, adding a control sample to the second reaction container comprising said enzyme and incubating said reaction containers; b) adding an aliquot from each reaction container to a unique reaction zone comprising a porous matrix comprising a substrate of said enzyme of a device, said substrate is a reporter, c) following incubating said device, exposing said reactions zones to a device that detects said reporter, and d) obtaining a value comprising the amount of reporter comprising a reaction zone, where an inhibitor is correlated with a lower amount of reporter. The data obtained from the reader can be assessed in a qualitative manner, that is, a visual inspection reveals an observable difference between a positive sample and a negative sample. In other embodiments, the signal obtained by the reader relating to the amount of reporter in a reaction zone is digitized and that data is processed to yield a quantitative value or can be processed to yield a metric, for example a normalized value that accounts for background levels and so on, as known in the art. Thus, in some embodiments, the data manipulation is one where the value from the sample is divided by the value of the background or of a negative control to yield a ratio or index, thus the reader obtained value is compared to a statistically determined ratio value cutoff, which can be a population mean value or a historical value determined by collating historical data, for determining or distinguishing a positive result from a negative result.

Figure 3:
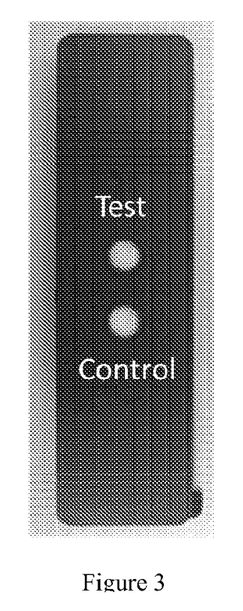
FIG. 3 shows an example of a test device with two wells functioning as reaction zones. Each well contains discs of the porous matrix which have been treated with an enzyme substrate or an indicator member of a reaction pair.]
Figure 4:
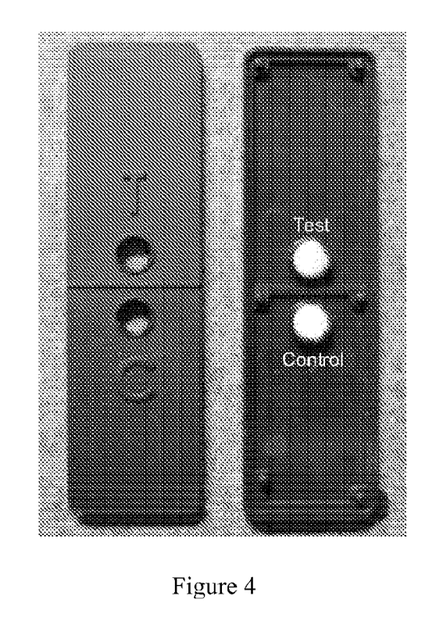
FIG. 4 shows an example of a test device composed of a top piece (left), labeled with, "T," for the test or experimental sample and, "C," for the control sample, and a bottom piece (right) containing two cylindrical wells functioning as reaction zones containing porous pads treated with enzyme substrate or a reagent. Once the top piece is assembled onto the bottom piece, the test device will look like that shown in FIG. 3.
Figure 5:
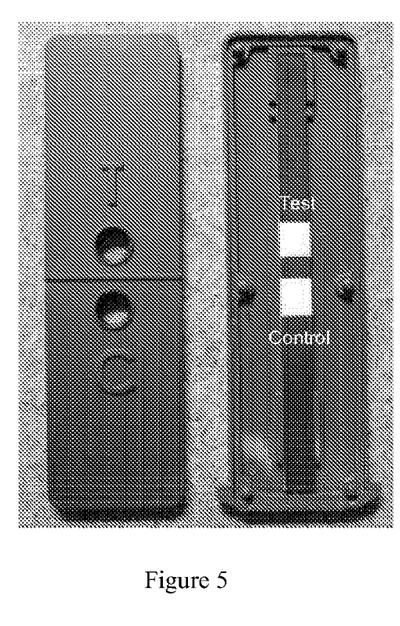
FIG. 5 shows an example of a test device composed of a top piece (left) and a bottom piece (right) containing a test strip to which are attached two pads treated with enzyme substrate or a reagent. These two pads function as reaction zones. Once the top piece is assembled onto the bottom piece, the test device will look like that shown in FIG. 3.
Figure 6:
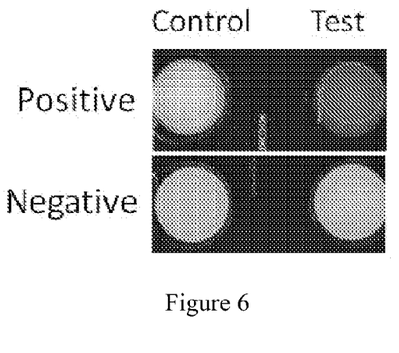
FIG. 6 provides examples of images of test results as captured by the reader. The top strip is an example of a positive test result. The bottom strip is an example of a negative test result.

FIGS. 3, 4, 5 provide further exemplifications of the test device via non-limiting examples. FIG. 3 presents one example of a test device referred to as a, "ticket," with the 2 reaction zones comprising 2 wells into which fluid can be added. FIG. 4 depicts one non-limiting example of a ticket assembly comprising a top and bottom piece. The top piece contains two openings and the bottom piece holds two porous discs treated with an enzyme substrate or a member of a reaction pair in 2 cylindrical wells. FIG. 5 presents another non-limiting example wherein the top piece of the ticket is similar to that shown in FIG. 4 and the bottom piece holds in place a longitudinal test strip to which two porous pads are attached. These porous pads are treated with an enzyme substrate or a member of a reaction pair. Upon assembly of the top piece onto the bottom piece, these two pads will be positioned directly under the two openings in top piece and will function as the reaction zones.

In addition to the test device and reader just described, the instant invention can comprise two separate containers with a limited and uniform amount of enzyme in each. The enzyme can be provided to the user in these containers in either liquid solution or as a dry reagent. Dry reagent can be prepared using lyophilization methods as required. The enzyme reagents are kept sealed in protective containers until a test is commenced.

The instant invention can comprise an onboard comparator which is the control reaction zone. The control reaction zone will contain the fluorescence, color, luminescence or other signal associated with a negative sample. The signal generated in the test sample reaction zone is compared to the signal at the control reaction zone. A significant difference in signal between these two reaction zones is evidence of a positive result, indicating that the test sample does contain an inhibitor at a greater than tolerable level.

The instant invention can comprise the following procedure. A measured and uniform volume of test sample fluid is added to one reagent container containing enzyme. The same measured and uniform volume of a negative fluid (control) is added to a second reagent container containing enzyme. In the case of enzyme that has been dried in these reagent containers, the addition of either test fluid or negative control fluid reconstitutes the enzyme. The reagent containers are then carefully shaken to mix the contents to ensure a homogeneous reaction mixture. The reaction mixtures are allowed to incubate for a sufficient amount of time to ensure that an inhibitor in the sample can react with and deactivate the active site of the enzyme.

After the prescribed inhibition period, the same volume of aliquot is removed from each of the reaction mixtures and transferred to their designated reaction zones on the test device. The enzyme in each reaction mixture then reacts with the substrate immobilized in the porous matrix in the test zone. After sufficient amount of time, the device is inserted into the reader. An onboard algorithm collects and transforms the signal into a ratio of the signal at the test reaction zone to that on the control zone.

The signal that is measured by the reader can be color, fluorescence or luminescence as determined by the enzyme-substrate reaction. The signal can be parsed into 6 possible channels, red, green, blue, hue, luminance and saturation. The numerical values associated with each channel can be used to generate a ratio of the test sample signal to the negative control signal. A channel or a combination of channels can be used to calculate a ratio result. The choice of channel(s) is dependent on the sensitivity the chosen channel(s) confers on the test.

The fluids that can be tested using the instant invention can be any liquid sample that can solubilize or suspend inhibitors. Non-limiting examples include water, blood fractions such as serum and plasma, cerebrospinal fluids, amniotic fluid, other physiological fluids and various solvents. The fluids can also comprise extracts of solid mixtures or gels to which inhibitors have been added, dispersed or encapsulated within. Such samples can be made compatible for analysis using the instant invention by appropriate extraction and clean-up procedures known in the art.

A, "reader," or, "reading device," comprises an electromechanical device that provides the ability to detect and to measure an appropriate signal, such as fluorescence, light, a color, and so on. A reader can comprise a sensing means for detecting a signal, such as a camera, a photomultiplier tube, a scanner, and so on. The reader can contain processor-controlled means to manipulate the sensing means, the sample or a carrier or holding means of one or more samples to enable detecting a plurality of sites or samples at one time or consecutively in a defined order. The reader can be configured as a component of a robotic system that introduces an article of manufacture that carries the sample, or the carrier, into the reading device, and then removes the article of manufacture when the detecting is completed. Spectrophotometers, fluorimeters, luminometers, and so on are examples of readers or reading devices.

The instant invention as applied to the detection of, for example, AChE inhibitors also can comprise the use of a test device in which reaction zones to which, for example, N-methylindoxyl acetate (NMI) has been immobilized. AChE enzyme is lyophilized in two reagent containers. For testing potable water samples, a negative water sample is used as the negative control. The test procedure follows the previously described steps.

The instant invention as applied to the detection of AChE inhibitors, further comprises a second set of reagents using a second enzyme, carboxylesterase (CE). CE is similarly lyophilized in two reagent containers. As previously described, AChE and CE can react with the same substrates, and in one embodiment for the detection of AChE inhibitors, can react with the same fluorogenic substrate, NMI, that is contained in the same test device. Whereas AChE is strongly reactive with most inhibitors such as organophosphates and carbamates but is weakly reactive with unoxidized organothiophosphates, CE can be inhibited by the organothiophosphate inhibitors without the need for oxidation and quenching, but is weakly reactive with other AChE inhibitors such as carbamates. Thus, by using these two sets of enzyme reagents, a test method for the detection of all AChE inhibitors can be produced that requires no oxidation and quenching steps. A positive result with one or both enzymes indicates the presence of an inhibitor in the test sample.

The total amount of time required to obtain a result using the instant invention can be shortened by exposing to elevated temperatures, for example, by heating the reagent containers after the test or control samples have been added to dissolve the lyophilized enzymes contained therein and mixed, or the device once the reaction mixture is added to the device, or by heating both the reagent containers and the device The containers holding the reaction mixtures or the device can be placed in a heating block, a water bath, an incubator, an oven, or be placed in contact with an appropriate heat source thereby accelerating the kinetics of reaction via the external heat energy applied. Other means to accelerate reaction kinetics and thereby to reduce the time to result include the addition to the reaction mixtures of a reagent that accelerates inhibitor/enzyme reaction kinetics in the reaction container. Examples of such reagents include, water soluble polymers, such as polyethylene glycol (PEG), polyethyleneoxide (PEO), poly(vinylalcohol), poly(vinylpyrrolidone), polyoxazoline, polymethyloxazoline, polyethyloxazoline, salts and other solutes that raise the activity of reactive compounds in solution.

By using the test device or ticket previously described to comprise 2 reaction zones containing a cholinesterase substrate, a rapid test to determine if esterase activity in an individual has been reduced due to exposure to and/or ingestion of inhibiting pesticides or nerve agents can be conducted. Blood, plasma, serum or other body fluid, collected, for example, via fingerstick or venipuncture from an individual (human or animal), or a medium or liquid holding a tissue sample of a patient is added to the test zone of the ticket while a control sample comprising the individual's corresponding blood, plasma or serum obtained prior to potential exposure is added to the control zone. Alternatively, a control sample comprising a blood, plasma, serum or solution comprising cholinesterase activity corresponding to the lower limit of the normal range can be added to the control zone. In other embodiments, a known positive sample or a known negative sample can be added to the control well of a device of interest. After sufficient incubation, the ticket can be examined or measured in a reader to determine if the signal generated in the test zone is significantly different from that generated in the control zone, which result indicates that the individual has been exposed to unhealthy levels of pesticides or nerve agents and is suffering from systemic cholinesterase inhibition. Such results can then be followed up with immediate treatment of the symptoms and the application of an antidote.

This method can be applicable for the detection of the inhibition of any endogenous enzyme found in any biological fluid.

It is within the skill of the artisan to determine the amount of enzyme to be placed in the reaction container or vessel, and the amount of substrate on the porous matrix of the test device as a design choice. For example, titration curves can be produced to determine the level of enzyme activity that can be detected. That can be compared to the anticipated enzyme levels found in an individual, or compared to the known toxicity levels of certain toxins. Based on those considerations, the amount of enzyme needed per reaction vial to obtain the level of sensitivity desired is determined.

Similarly, and/or based on those considerations, the amount of substrate to be immobilized can be determined. The amount can take into account any inactivation by the immobilization process and may be in excess to ensure the likelihood of obtaining a signal at lower levels of uninhibited enzyme.

The substrate can be applied to the porous matrix directly or indirectly as known in the art. Hence, a solution of substrate can be applied to the porous matrix and then the matrix is dried. A linker or a molecule that binds substrate can be applied to the porous matrix, such as by drying or using a chemical process, such as, derivatizing the matrix to enable binding of the linker or binding molecule thereto to yield a modified porous matrix, which modified matrix then is exposed to the substrate to enable the substrate to be bound by the linker or binding molecule.

As to the enzyme, such are commercially available in dry form and thus can be added directly to the reaction vessel. Any buffer salts, proteins, stabilizers and the like can be added to the container. In embodiments, the enzyme or necessary reagent is in liquid form. Thus, the liquid reagent and any other reagents as needed are added to the reaction vessel. The reaction container is stored under the preferred conditions to retain enzyme activity.

The materials and methods of interest now will be exemplified in the following non-limiting examples.

EXAMPLES

Example 1 Preparation and Treatment of Porous Matrix with NMI Substrate

Filter discs (3/16" diameter) of porous matrix Surewick Sample Pad C248 SA3J035V06 (Millipore). were punched from sheets using a manual punch and die. An average weight of 12.92 mg per disc was determined by weighing 50 filter discs on an analytical balance. Filter discs (25.2 g for a total of 1950 pads by weight) were placed in a clean 1 liter glass beaker.

N-methyl indoxyl (NMI) acetate (100 mg, Sigma-Aldrich) was dissolved in 100 mL 200 proof (100%) USP ethyl alcohol (Sigma-Aldrich) for a final concentration of 1 mg/mL and added to the beaker containing the filter pads. The filter discs were mixed gently with a spatula for five minutes. The discs were then carefully removed from the solution and spread out on a polystyrene sheet and dried at 45° C. for two hours. The filter discs were then removed from the oven and stored in a resealable plastic bag with desiccant.

Example 2 Preparation of Lyophilized AChE

AChE from eel (Sigma-Aldrich) was dissolved to a final concentration of 0.32 units/mL in a buffer containing 10 mM potassium phosphate, 5% sucrose and 0.5% BSA at pH=7.4 and filtered with a 0.22 μm filter. Aliquots (0.5 mL) were lyophilized in 2 mL amber glass vials from Kimble Chase. The vials were sealed with 2 leg butyrate lyophilization stoppers and aluminum crimp seals from Wheaton.

Example 3 Preparation of Lyophilized Carboxylesterase (CE)

CE from rabbit liver (Sigma-Aldrich) was dissolved to a final concentration of 0.2 units/mL in a buffer containing 10 mM potassium phosphate, 5% sucrose and 0.5% BSA at pH=7.4 and filtered with a 0.22 μm filter. Aliquots (0.5 mL) were lyophilized in 2 mL, amber glass vials from Kimble Chase. The vials were sealed with 2 leg butyrate lyophilization stoppers and aluminum crimp seals from Wheaton.

Example 4 Detection of AChE Inhibitors

Pairs of NMI substrate discs were placed into each of 2 wells in black test devices referred to as, "tickets." The discs contained in the wells comprise the reaction zones on the tickets (FIGS. 3 and 4). One disc was used for a negative control sample, the other disc was used for the test sample. Stock solutions (1 mg/mL) of the carbamate pesticides, oxamyl and aldicarb (Supelco), were prepared in methanol, then serially diluted in purified water. A 1 mL volume of each dilution was added to a vial of the lyophilized AChE. As a negative control, 1 mL of purified water was added to another vial of lyophilized AChE. The vials were stoppered, given a brief mix on a vortexer and allowed to incubate for 30 minutes.

After the 30 minute incubation step, 50 µL of the negative control reaction mixture was added to the NMI substrate disc marked "C" (for Control) on the ticket. Similarly, 50 µL of the test sample reaction mixture containing pesticide was added to the NMI substrate disc marked "T" (for Test) on the test device (FIG. 3).

Figure 1:
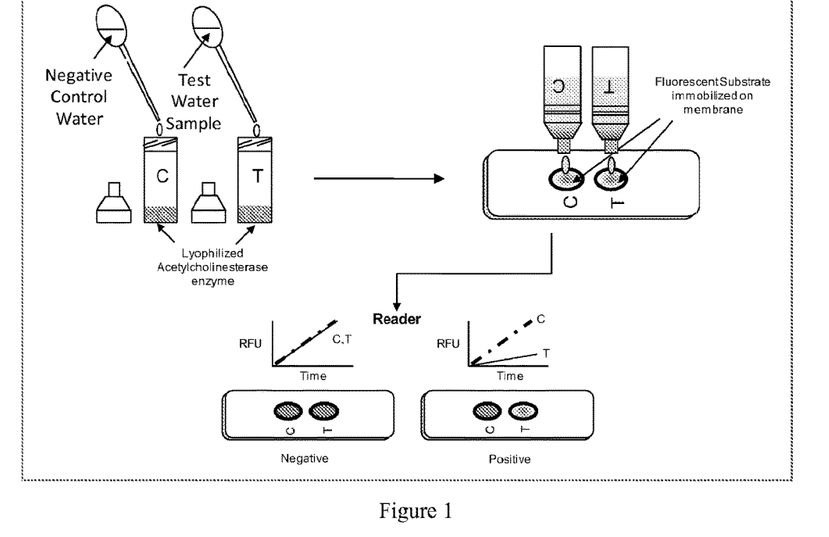
Figure 2:
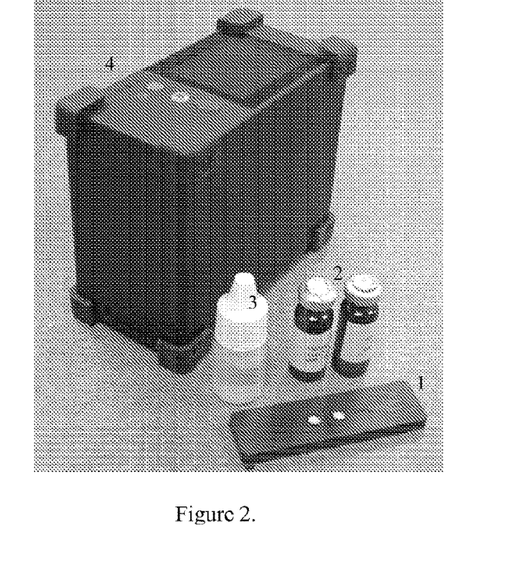

The tickets were allowed to react for 15 minutes at room temperature and then inserted into the handheld fluorescence reader comprised of low light color cameras, 400 nm UV LED and custom color analysis software (FIG. 2). Enzyme inhibition was detected by the difference in the hue measurement of the Test Sample compared to the negative control (FIG. 4). The reader calculates a ratio of the hue measured in the test sample well to the hue measured in the negative control well. Based on a statistical calculation of total system error, a ratio greater than 1.25 is considered positive.

Figure 7:
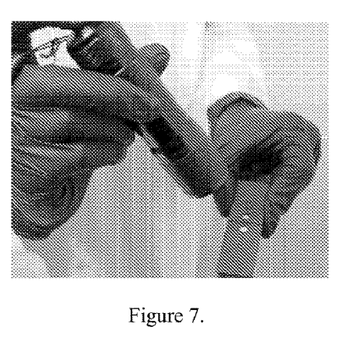
FIG. 7 depicts the use of an LED flashlight instead of a handheld reader to determine results from the test.
Figure 8:
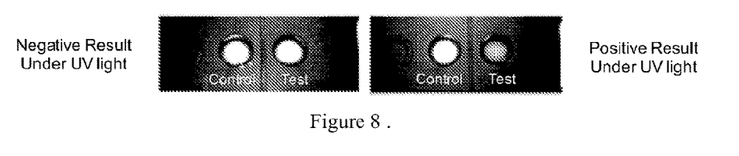
FIG. 8 shows typical results under the illumination of an LED.

It was found that inhibition of the enzyme, demonstrated by the lack of formation of the highly fluorescent product, N-methyl-3-hydroxyindole, could be detected visually under UV flashlight illumination as well. Analysis was alternatively performed by visual observation of the ticket using a 400 nm UV LED flashlight (FIGS. 7 and 8). Visually, inhibition was detected directly based on the decrease in fluorescence of the test sample compared to the negative control.

In a similar fashion, the organophosphate pesticides that may require an oxidation step to be detectable in vitro such as, methyl parathion, fenamiphos and methamidiphos were tested using vials containing the lyophilized CE instead of AChE. The test procedure when using the lyophilized CE reaction containers was exactly the same as that used with the lyophilized AChE reaction containers. There is no sample oxidation required.

Table 1 exemplifies results obtained when testing water containing pesticides at an amount that approximates the Human Lethal Concentration (HLC) of each. Aldicarb and oxamyl are carbamates that react strongly with AChE while methyl parathion, fenamiphos and methamidophos are organothiophosphate pesticides that, without oxidation, react more strongly with CE than with AChE. A positive result with either enzyme indicates the presence of an inhibitor in the sample

TABLE 1

Results using a test sample well:control well hue ratio cutoff of 1.25 in the rapid test for AChE inhibitors. The data are that of the reader,. A positive result with at least one enzyme is considered a positive result indicating the presence of an inhibitor.

| Pesticide | mg/L | AChE hue ratio | Result | CE hue ratio | Result |
|---|---|---|---|---|---|
| Aldicarb | 0.17 | 1.56 | Positive | 1.02 | Negative |
| Oxamyl | 0.032 | 1.61 | Positive | 1.03 | Negative |
| Methyl Parathion | 33.6 | 1.62 | Positive | 2.04 | Positive |
| Fenamiphos | 0.56 | 0.97 | Negative | 2.14 | Positive |
| Methamidophos | 1.4 | 1.27 | Positive | 2.04 | Positive |

Example 5 Shorter Time to Result with Heating

Water obtained from reverse osmosis treatment was spiked with 0.1 ppm oxamyl, a carbamate pesticide. The pesticide-contaminated sample was tested using the procedure described in Example 4. Two sets of two reagent vials containing AChE were opened. To the first vial of each set was added 1 mL of the test sample containing pesticide. To the second vial of each set was added 1 mL of a negative control water. All vials were thoroughly mixed. One set of vials was placed in a heating block set at 40° C., while the other set of vials was allowed to stand at room temperature (21° C.). From each set of vials, 50 µL was sampled at 5, 10, 15, and 20 minutes and transferred to corresponding reaction zones in test tickets. After 15 minutes incubation, the fluorescence in the reaction zones of each ticket were measured on a reader. The results summarized in Table 2 show that heating the reaction vials enabled the earlier detection of a positive sample.

TABLE 2

Effect of Heating on Time of Detection of a Positive Sample

| Heating Time (min) | Not Heated | Heated |
|---|---|---|
| 5 | negative | positive |
| 10 | negative | positive |
| 15 | positive | positive |
| 20 | positive | positive |

Example 6 Detection of Cholinesterase Inhibition in Human Plasma

An aliquot of a human plasma pool was spiked with 10 ppt oxamyl and serially diluted with the same human plasma pool to a final 100 ppm oxamyl concentration. The sample was then allowed to incubate overnight (22 hours) at room temperature to allow cholinesterase inhibition to take place. The spiked sample would represent plasma from an individual who had ingested an inhibiting pesticide or nerve agent. The spiked sample (50 µL) was then added to the test zone "T" of a ticket (FIG. 3). To the control zone "C" was added the unspiked human plasma pool. For comparison, a separate ticket was run using the unspiked pool as both the test sample and the control to represent an unexposed individual. The results obtained show that the signal developed in the test zone containing the spiked sample was significantly reduced compared to the control zone, resulting in a hue ratio of 3.10, while the unspiked sample was negative with a hue ratio of 1.03.

All references cited herein are herein incorporated by reference in entirety.

REFERENCES

Mahajna Mahmoud and Casida John E "Oxidative Bioactivation of Methamidophos Insecticide: Synthesis of N-Hydroxymethamidophos (A Candidate Metabolite) and its Proposed Alternative Reactions Involving N→O Rearrangement or Fragmentation through a Metaphosphate Analogue", Chem. Res. Toxicol, 11, 26-34, 1998

Özlem Faizl, Ahmet Colakl, Nagihan Saglam, Sabriye Çanakçi and Ali Osman Beldüz. 2007 "Determination and Characterization of Thermostable Esterolytic Activity from a Novel Thermophilic *Bacterium Anoxybacillus* gonensis A4", Journal of Biochemistry and Molecular Biology, Vol. 40, No. 4, July 2007, pp. 588-594

Timo Hamers, Kim R. J. Molin, Jan H. Koeman, and Albertinka J. Murk "A Small-Volume Bioassay for the Quantification of the Esterase Inhibiting Potency of Mixtures of Organophosphate and Carbamate Insecticides in Rainwater: Development and Optimization", Toxilogical Sciences, 58, 60-67 (2000)

Craig E. Wheelock, Guormin Shan and James Ottea "Overview of Carboxylesterases and Their Role in the Metabolism of Insecticides", J. Pestic. Sci., 30(2), 75-83 (2005)

Craig E. Wheelock, Bryn M. Phillips, Brian S. Anderson, Jeff L. Miller, Mike J. Miller, and Bruce D. Hammock, D. M. Whitacre (ed.), "Applications of Carboxylesterase Activity in Environmental Monitoring and Toxicity Identification Evaluations (TIEs)", Reviews of Environmental Contamination and Toxicology. 117-178 © Springer 2008

Yuske Amaki, Edgard E. Tulin, Shunsaku Ueda, Kuio Ohmiya, and Tsunco Yamane "Purification and Properties of a Thermostable Esterase of *Bacillus stearothermophilus* Produced by recombinant *Bacillus brevis*", Biosci. Biotech. Biochem., 56 (2), 238-241, 1992

"Techniques to Detect Insecticide Resistance Mechanisms (Field and Laboratory Manual)", WHO/CDS/CPC/MAL/98.6, World Health Organization Department of Disease Prevention & Control WHO Communicable Diseases (CDS)

Cheryl L. Beseler, Lorann Stallones, Jane A. Hoppin, Michael C. R. Alavanja, Aaron Blair, Thomas Keefe, and Freya Kamel "Depression and Pesticide Exposures among Private Pesticide Applicators Enrolled in the Agricultural Health Study" Environmental Health Perspectives 116, 1713-1719, 2008

Wang A, Costello S, Cockburn M, Zhang X, Bronstein J and Ritz B. "Parkinson' disease risk from ambient exposure to pesticides." Eur. J. Epidemiol. 26(7), 547-55, 2011

Elbaz A, Clavel J, Rathouz P J, Moisan F, Galanaud J P, Delemotte B, Alperovitch A, Tzourio C. "Professional exposure to pesticides and Parkinson's disease" Ann Neurol. 22(4), 494-504, 2009

We claim:

1. A system for detecting presence of an inhibitor of an esterase comprising:
   a) a self-calibrated, modular, handheld device comprising a top piece and a bottom piece, said bottom piece comprising a negative control reaction zone and a test reaction zone for a test sample suspected of comprising an inhibitor of an esterase; each reaction zone comprising a porous matrix consisting essentially of an immobilized substrate of said esterase, each reaction zone positioned below an opening in said top piece when said top piece is assembled on said bottom piece; and said negative control reaction zone and said test reaction zone are separate and exclusive; wherein in a reaction of said substrate and said esterase, a product of said reaction comprises a detectable reporter; and wherein a negative control reaction zone comprising a negative control sample comprises detectable reporter; and
   b) separate from said device, two reaction containers, each container comprising a same amount of said esterase, and optionally,
   c) separate from said device, a reader that detects said detectable reporter.

2. The system of claim 1, wherein said esterase comprises a cholinesterase.

3. The system of claim 1, wherein said esterase comprises an acetylcholinesterase, a butylcholinesterase or a carboxylesterase.

4. The system of claim 1, wherein said substrate comprises an N-methylindoxyl acetate.

5. The system of claim 1, wherein said inhibitor comprises an organophosphate, an organothiophosphate, an organophosphonate or a carbamate.

6. The system of claim 1, wherein said inhibitor comprises a pesticide, a toxicant or a nerve agent.

7. The system of claim 1, wherein one of said two reaction containers comprising said test sample comprises a liquid sample.

8. The system of claim 7, wherein said liquid sample comprises a water for human consumption, a source water from natural or man-made bodies of water, an ocean, a wash of an edible product or a solution comprising a wipe of a surface.

9. The system of claim 1, wherein each of said two reaction containers is free of an oxidizing agent.

10. The system of claim 1, wherein each of said two reaction containers comprises a reagent that accelerates inhibitor/esterase reaction kinetics.

11. A method for detecting presence of an inhibitor of an esterase comprising:
    a) adding an aliquot of a test sample suspected of comprising said inhibitor of said esterase to a first reaction container comprising an amount of said esterase of claim 1 and forming a solution, adding a negative control sample to a second reaction container comprising said amount of said esterase of claim 1 and forming a solution, and incubating said solutions in said reaction containers;
    b) adding an aliquot of solution of said first reaction container of step a) to said test reaction zone of said device of claim 1 and an aliquot of solution of said second reaction container of step a) to said negative control reaction zone of said device of claim 1; and
    c) determining presence of detectable reporter in said test reaction zone and in said negative control reaction zone; wherein said negative control reaction zone comprises detectable reporter, and a reduced level of detectable reporter in said test reaction zone correlates with presence of said inhibitor in said test sample.

12. The method of claim 11, wherein said determining step comprises exposing said reaction zones to a detecting device that detects said reporter to obtain a value comprising amount of reporter in a reaction zone.

13. The method of claim 11, wherein incubating said test sample or said control sample with said esterase of step a) is in absence of an oxidizing agent.

14. The method of claim 12, wherein said detecting device obtained value is compared to a statistically determined ratio value cutoff determining a positive result from a negative result, said ratio comprising value of reporter comprising said first reaction zone divided by value of reporter comprising said second reaction zone.

15. The method of claim 12, wherein said detecting device comprises an illuminating device.

16. The method of claim 11, wherein said reaction containers of step a) comprise a reagent to accelerate reaction kinetics of said inhibitor and said esterase.

17. A method for detecting reduced activity of an esterase exposed to an inhibitor comprising:
    a) adding an aliquot of a test sample suspected of comprising said esterase exposed to said inhibitor to said test reaction zone of said device of claim 1 and an aliquot of a negative control sample comprising said esterase to said negative control reaction zone of said device of claim 1; and b) determining presence of detectable reporter in said test reaction zone and in said negative control reaction zone; wherein said negative control reaction zone comprises detectable reporter, and a reduced amount of detectable reporter in said test reaction zone correlates with esterase exposed to said inhibitor.

18. The method of claim 17, wherein said test sample, said control sample or both comprise a biological fluid of an individual.

19. The method of claim 17, wherein said determining comprises a detecting device that detects said reporter.

20. The method of claim 17, wherein said control sample comprises a biological fluid from an individual prior to exposure of said individual to said inhibitor of said esterase.

21. The system of claim 1, wherein said esterase further comprises an additional esterase.

22. The system of claim 21, comprising an acetylcholinesterase and a carboxylesterase.

23. The system of claim 1, wherein said esterase reacts with an oxidized inhibitor.

24. The system of claim 1, wherein said esterase reacts with an unoxidized inhibitor.

25. The method of claim 11, wherein said esterase further comprises an additional esterase.

26. The method of claim 25, comprising an acetylcholinesterase and a carboxylesterase.

27. The method of claim 11, wherein said esterase reacts with an oxidized inhibitor.

28. The method of claim 11, wherein said esterase reacts with an unoxidized inhibitor.

* * * * *